US008110284B2

(12) United States Patent
Naigertsik et al.

(10) Patent No.: US 8,110,284 B2
(45) Date of Patent: Feb. 7, 2012

(54) MICROCAPSULES LOADED WITH ACTIVE INGREDIENTS AND A METHOD FOR THEIR PREPARATION

(75) Inventors: Oleg Naigertsik, Haifa (IL); Sorel Rothschild, Jerusalem (IL); Claudio Rottman, Modiin (IL)

(73) Assignee: Sol-Gel Technologies Ltd., Beit Shemesh (IL)

( * ) Notice: Subject to any disclaimer, the term of this patent is extended or adjusted under 35 U.S.C. 154(b) by 1278 days.

(21) Appl. No.: 10/566,369

(22) PCT Filed: Aug. 1, 2004

(86) PCT No.: PCT/IL2004/000702
§ 371 (c)(1),
(2), (4) Date: Jan. 30, 2006

(87) PCT Pub. No.: WO2005/009604
PCT Pub. Date: Feb. 3, 2005

(65) Prior Publication Data
US 2007/0292676 A1    Dec. 20, 2007

Related U.S. Application Data

(60) Provisional application No. 60/491,295, filed on Jul. 31, 2003.

(51) Int. Cl.
*B01J 13/18* (2006.01)
*A61K 8/18* (2006.01)
*A61K 8/44* (2006.01)
*A61Q 17/04* (2006.01)

(52) U.S. Cl. ............ 428/321.1; 428/321.5; 424/59; 424/60; 264/4.7

(58) Field of Classification Search ............ 424/59, 424/60; 428/321.1, 321.5; 264/4.7
See application file for complete search history.

(56) References Cited

U.S. PATENT DOCUMENTS

| | | |
|---|---|---|
| 2,885,366 A | 5/1959 | Iller |
| 3,785,798 A | 1/1974 | Horai et al. |
| 3,826,670 A | 7/1974 | Rees |
| 4,069,311 A | 1/1978 | Mannara |
| 4,129,645 A | 12/1978 | Barnett et al. |
| 4,169,069 A | 9/1979 | Unger et al. |
| 4,349,456 A | 9/1982 | Sowman |
| 4,444,746 A | 4/1984 | Harvey et al. |
| 4,464,317 A | 8/1984 | Thies et al. |
| 4,533,484 A | 8/1985 | Walles et al. |
| 4,606,913 A | 8/1986 | Aronson et al. |
| 4,671,956 A | 6/1987 | Bouillon et al. |
| 4,769,080 A | 9/1988 | Clark et al. |
| 4,891,211 A | 1/1990 | Winston |
| 4,931,362 A | 6/1990 | Zsifkovits et al. |
| 4,988,744 A | 1/1991 | Yamamoto |
| 5,165,914 A | 11/1992 | Vlock |
| 5,200,334 A | 4/1993 | Dunn et al. |
| 5,269,840 A | 12/1993 | Morris et al. |
| 5,292,801 A | 3/1994 | Avnir et al. |
| 5,387,622 A | 2/1995 | Yamamoto |
| 5,455,048 A | 10/1995 | Lahmani et al. |
| 5,500,223 A | 3/1996 | Behan et al. |
| 5,520,917 A | 5/1996 | Mizuguchi et al. |
| 5,556,617 A | 9/1996 | Ribier et al. |
| 5,587,170 A | 12/1996 | Caisey et al. |
| 5,591,453 A | 1/1997 | Ducheyne et al. |
| 5,607,664 A | 3/1997 | Ascione et al. |
| 5,650,311 A | 7/1997 | Avnir et al. |
| 5,670,209 A | 9/1997 | Wyckoff |
| 5,672,301 A | 9/1997 | Orly et al. |
| 5,691,060 A | 11/1997 | Levy |
| 5,739,020 A | 4/1998 | Pope |
| 5,756,073 A | 5/1998 | Miller et al. |
| 5,785,977 A | 7/1998 | Breithbarth |
| 5,876,701 A | 3/1999 | Wong et al. |
| 5,879,716 A | 3/1999 | Katz et al. |
| 5,895,757 A | 4/1999 | Pope |
| 5,912,016 A | 6/1999 | Perrier et al. |
| 5,914,101 A | 6/1999 | Tapley et al. |
| 6,037,000 A | 3/2000 | Chang et al. |
| 6,074,629 A | 6/2000 | Kostinko et al. |
| 6,077,522 A | 6/2000 | Scher et al. |
| 6,090,399 A | 7/2000 | Ghosh et al. |

(Continued)

FOREIGN PATENT DOCUMENTS

AU        764016 B2    5/2000

(Continued)

OTHER PUBLICATIONS

Dai Duyan, "A Study on the Technique and the Application of Preparing Microcapsules," Journal of Tianjin Institute of Textile Science and Technology, vol. 14, No. 1, pp. 95-101 (1994).
Aizawa et al., "Preparation of Spherical Hydrous Silica Oxide Particles under Acidic Condition via Sol-Gel Processing," Journal of Sol-Gel Science and Technology 19, 329-332, 2000.
Avnir et al., "Organic Fluorescent Dyes Trapped in Silica and Silica-Titania Thin Films by the Sol-Gel Method Photophysical, Film and Cage Properties," Journal of Non-Crystalline Solids 74, (1985), 395-406.
Barbe et al., "Sol-Gel Microspheres and Nanospheres for Controlled Release Applications," Controlled Release Society 29th Annual Meeting Proceedings, #293, 545-546.
Butler et al., "An emulsion method for producing fine, low density, high surface area silica powder from alkoxides," Journal of Materials Science 31, (1996), 1675-1680.
Federal Register, vol. 67, No. 94, 34616-34620.

(Continued)

*Primary Examiner* — Thao T. Tran
(74) *Attorney, Agent, or Firm* — Lowe Hauptman Ham & Berner LLP

(57) ABSTRACT

The invention relates to microcapsules having a core material encapsulated within a microcapsular shell, the core material comprises at least one active ingredient, wherein the microcapsular shell comprises at least one inorganic polymer comprising polymerized precursors obtained by in-situ polymerization of the precursors; wherein the concentration of the core material based total weight of the microcapsules is above 95% w/w. The invention further relates to a composition and to a suspension comprising the microcapsules. The invention additionally relates to a process for preparing the microcapsules.

33 Claims, No Drawings

U.S. PATENT DOCUMENTS

| | | | |
|---|---|---|---|
| 6,132,773 | A | 10/2000 | Amiche |
| 6,143,280 | A | 11/2000 | Pike et al. |
| 6,159,453 | A | 12/2000 | Avnir et al. |
| 6,197,757 | B1 | 3/2001 | Perrier et al. |
| 6,238,650 | B1 | 5/2001 | Lapidot et al. |
| 6,242,099 | B1 | 6/2001 | Grandmontagne et al. |
| 6,251,313 | B1 | 6/2001 | Deubzer et al. |
| 6,280,746 | B1 | 8/2001 | Arquette et al. |
| 6,303,149 | B1 | 10/2001 | Magdassi et al. |
| 6,315,986 | B1 | 11/2001 | Wong et al. |
| 6,337,089 | B1 | 1/2002 | Yoshioka et al. |
| 6,365,642 | B1 | 4/2002 | Dyer et al. |
| 6,436,375 | B1 | 8/2002 | Lapidot et al. |
| 6,468,509 | B2 | 10/2002 | Lapidot et al. |
| 6,495,352 | B1 | 12/2002 | Brinker et al. |
| 6,607,713 | B1 | 8/2003 | Chodorowski et al. |
| 6,616,947 | B1 | 9/2003 | Depuis |
| 6,703,032 | B2 | 3/2004 | Gers-Barlag et al. |
| 6,855,335 | B2 | 2/2005 | Seok et al. |
| 2002/0064541 | A1* | 5/2002 | Lapidot et al. ............. 424/401 |
| 2005/0037087 | A1 | 2/2005 | Lapidot et al. |
| 2005/0208134 | A1 | 9/2005 | Magdassi et al. |
| 2006/0251687 | A1 | 11/2006 | Lapidot et al. |

FOREIGN PATENT DOCUMENTS

| | | |
|---|---|---|
| DE | 19811900 | 9/1999 |
| EP | 0281034 | 9/1988 |
| EP | 0 462 388 A2 | 6/1990 |
| EP | 0581651 | 2/1994 |
| EP | 0 680 753 A2 | 11/1995 |
| EP | 0934773 | 8/1999 |
| EP | 0 972 563 A1 | 1/2000 |
| FR | 2703927 | 10/1994 |
| FR | 2774906 | 8/1999 |
| FR | 2780901 | 1/2000 |
| GB | 1319991 | 6/1973 |
| GB | 2416524 | 2/2006 |
| JP | 01-113436 A | 5/1989 |
| JP | 2-2867 | 1/1990 |
| JP | 02-040302 A | 2/1990 |
| JP | 2-251240 | 10/1990 |
| JP | 03-229634 A | 10/1991 |
| JP | 07-173452 A | 7/1995 |
| JP | 7-238983 | 9/1995 |
| JP | 09-110463 A | 4/1997 |
| JP | 9235217 | 9/1997 |
| WO | 94/04261 A1 | 3/1994 |
| WO | 97/18267 | 5/1997 |
| WO | 97/45367 A1 | 12/1997 |
| WO | 98/15183 A1 | 4/1998 |
| WO | 98/31333 | 7/1998 |
| WO | 99/03450 A1 | 1/1999 |
| WO | 00/09652 | 2/2000 |
| WO | 0025761 | 5/2000 |
| WO | 00/47236 A1 | 8/2000 |
| WO | 00/71084 | 11/2000 |
| WO | 00/72806 | 12/2000 |
| WO | 01/12221 A1 | 2/2001 |
| WO | 01/13924 A1 | 3/2001 |
| WO | 01/80823 | 11/2001 |
| WO | 02/085113 A1 | 10/2002 |
| WO | 03/034979 | 5/2003 |
| WO | 03/039510 | 5/2003 |
| WO | 03/066209 | 8/2003 |
| WO | 2004/069216 | 8/2004 |
| WO | 2004/081222 | 9/2004 |
| WO | 2007/000316 A1 | 1/2007 |
| WO | 2007/015243 A2 | 2/2007 |
| WO | 2007/036939 A2 | 4/2007 |
| WO | 2008/002637 A2 | 1/2008 |
| WO | 2008/072239 A2 | 6/2008 |
| WO | 2008/093346 A2 | 8/2008 |
| WO | 2008/093347 A2 | 8/2008 |

OTHER PUBLICATIONS

Hou et al., "Improvement of photofatigue resistance of spirooxazine entrapped in organic-inorganic composite synthesized via the sol-gel process," SPIE, vol. 2288 Sol-Gel Optics III, (1994), 328-339.

Nakatsuka, "Surface Modification of Inorganic Pigments with Organic UV Absorbers," Colloids and Surfaces 34, (1988/89), 323-324.

Tatapudy et al., "Benzoyl Peroxide Microcapsules I. Preparation of Core Material," Indian Drugs 32(6), (1995), 239-248.

Midmore, B.R., "Preparation of a Novel Silica-Stabilized Oil/Water Emulsion" Colloids and Surfaces A: Physicochemical and Engineering Aspects, vol. 132, pp. 257-265 (1998).

Bugnon, P, "Surface treatment of pigments. Treatment with inorganic materials", Progress in Organic Coatings, vol. 29, pp. 39-43, (1996).

Hall, S.B., et al., "Cocondensation of Organosilica Hybrid Shells on Nanoparticle Templates: A Direct Synthetic Route to Functionalized Core—Shell Colloids",Langmuir, vol. 16, pp. 1454-1456, (2000).

Haq, I., et al., "Preparation and properties of uniform coated inorganic colloidal particles 9. Titania on copper compouns", Colloids and Surfaces A: Physicochemical and Engineering Aspects, vol. 81, pp. 153-159, (1993).

Hench, L.L., et al., "The Sol-Gel Process",Chem. Rev. vol. 90, pp. 33-72, (1990).

Hsu, W.P., et al., "Paper Whiteners I. Titania Coated Silica", Journal of Colloid and Interface Science, vol. 156, pp. 56-65, (1993).

Iler, R., "Silica Gels", The Chemistry of Silica, pp. 510-533, (1979).

Kumar, M.N.V. Ravi, "Nano and Microparticles as Controlled Drug Delivery Devices", J. Pharm. Pharmaceutic. Sci. 3(2)234-258, (2000).

Lapidot, N., et al., "Advanced Sunscreens: UV Absorbers Encapsulated in Sol-Gel Glass Microcapsules", Journal of Sol-Gel Science and Technology, vol. 26, pp. 67-72, (2003).

Magdassi, S., et al. Cosmeceutics and Delivery Systems in Novel Cosmetics Delviery System, S. Magdassi, E. Touitou Eds., Dekker inc., (1999).

Matijevic, E., et al, "Note Coating of Nanosize Silver Particles with Silica", Journal of Colloid and Interface Science, vol. 221, pp. 133-136, (2000).

Mikrajuddin, F., et al., "Stable photoluminescence of zinc oxide quantum dots in silica nanoparticles matrix prepared by the combined sol-gel and spray drying method", Journal of Applied Physics, vol. 89, pp. 6431-6434, (2001).

Nakatsuka, et al., "Surface Modification of Inorganic Pigments with Organic UV Absorbers",Colloid and Surfaces, vol. 34, pp. 323-334, (1988/89).

Osseo-Asare, K., "Hydrolysis of Silicon Alkoxides in Microemlsions", Surfactan Sci. Sek., vol. 42, pp. 147-188, (2000).

Rottman, C., et al, "Advanced Sunscreens: UV Absorbers Entrapped in Glass Microcapsules", Euro Cosmetics, pp. 20-22, (2000).

Rottman, C., et al. "Sol-Gel Products News: Advanced Sunscreen: UV Absorbers Entrapped in Sol-Gel Glass Microcapsules", Journal of Sol-Gel Science and Technology, vol. 23, pp. 268-270, (2002).

M.P.B van Bruggen, "Preparation and Properties of colloidal Core-Shell Rods with Adjustable Aspect Ratios", Langmuir, vol. 14, pp. 2245-2255, (1998).

Sol-Gel Science, The Physics and Chemistry of Sol-Gel Processing, C. Jeffrey Brinker, George W. Scherer, May 1990, (pp. 562-563).

Iqball Gill et al. "Encapsulation of Biologicals within Silicate, Siloxane, and Hybrid Sol-Gel Polymers: An Efficient and Generic Approach", J. Am. Chem. Soc. vol. 120, pp. 8587-8598, (1998).

* cited by examiner

US 8,110,284 B2

MICROCAPSULES LOADED WITH ACTIVE INGREDIENTS AND A METHOD FOR THEIR PREPARATION

RELATED APPLICATIONS

The present application is based on International Application PCT/IL2004/000702 filed Aug. 1, 2004, and claims priority from, U.S. Provisional Application No. 60/491,295, filed Jul. 31, 2003, the disclosure of which is hereby incorporated by reference herein in its entirety.

FIELD OF THE INVENTION

The present invention generally relates to microcapsules, compositions comprising the microcapsules and to a method for their preparation.

BACKGROUND OF THE INVENTION

Isolating functional molecules or substances in inert materials has many useful benefits and applications where chemical contact between the active ingredient and the immediate environment should be minimized. For example, make-up compositions, such as make-up colors are currently using a very limited number of approved natural pigments and even fewer artificial organic colors. Many dyes and pigments with desired color shades of natural or synthetic origin are not approved for skin contact because their safety for direct skin contact has not been demonstrated. Isolating the colorants in a transparent and inert isolating material provides a way to prevent the direct contact between the color molecules and the skin, while retaining (or even enhancing) the color intensity. Another very important application is in sunscreen compositions. The active ingredients in sunscreens have been reported to cause contact dermatitis and may cause photo contact dermatitis. Moreover, the light-excited species of these reagents may undergo photodecomposition reactions resulting in the production of free radicals and reactive oxygen species, which may bear deleterious effects on live tissues. Thus, encapsulating sunscreen active ingredients by enveloping them within a transparent silica shell offers a sophisticated way to benefit from the light-absorbing capability of sunscreens, while substantially isolating them and/or their possible photodecomposition products from the live tissues. Another example, from a totally different field, is the encapsulating of food colors either for prolonging the shelf life of food products containing unstable natural colors such as lycopene and carotene or for isolating artificial food colors that have undesirable side effects. Encapsulating food colors of the second type in inert transparent microcapsules provides a way to prevent the digestion of these colorants while maintaining their desired color effect.

U.S. Pat. Nos. 6,303,149, 6,238,650, 6,468,509, 6,436,375 and International publication Nos. WO 01/80823, WO 03/034979 and WO 03/039510 (the disclosures of these patents and publications are incorporated herein by reference in their entirety), disclose sol-gel microcapsules and methods for their preparation. In these patents and publications the loading of the active ingredients (termed also "functional molecules") which constitutes the core of the microcapsules is up to 95% (w/w).

U.S. Pat. No. 6,365,642 discloses a process for obtaining open-celled foams by polymerizing a high internal phase (water-in-oil) emulsion, which has small amount of a continuous oil phase and a relatively greater amount of discontinuous phase. The water-in-oil emulsion taught cannot be used to form sol-gel microcapsules since the oil constitutes the external phase.

EP 0934 773 relates to microcapsules, wherein the capsule wall is composed of organopolysiloxane, and to a method for producing such micro capsules.

There is a widely recognized need and it will be highly advantageous to have microcapsules comprising a high concentration (above 95% w/w) of the core material (which includes the active ingredient) and yet which is capable of minimizing the contact between the active ingredient and the environment. Such high concentration of the core material is required, for example, in order to obtain high Sun Protection Factor (SPF) values, or in many other applications where high loading of an encapsulated active ingredient in the composition is required.

Additionally it will be highly advantageous to have an efficient encapsulation method which is simplified in production lower in cost (i.e involving less monomer and less waste disposal) and which is capable of having high concentrations (above 95% w/w) of the core material (active ingredient) and yet preventing the leaching of the active ingredient from the microcapsules. Such a method will facilitate the encapsulation of a wide variety of molecules or substances, where the application may demand high loading of the encapsulated molecules or substances.

Moreover, it will be highly advantageous to have an oil-in-water emulsion having a high concentration (above 50%) of the internal oily phase and to have emulsions which is simplified in production.

DEFINITIONS

In the present invention the term "core material" refers to the inside part of the microcapsules comprising an active ingredient that is surrounded by the shell of the microcapsules. This term refers to any material present in the core, both the active ingredient and the excipients such as the liquid carrier.

In the present invention, the term "precursor" refers to any metal or semi-metal organo-metallic monomer, or a prepolymer (which means several monomers polymerized together) thereof, which allows to obtain a glass or ceramic material by in-situ polymerization (an inorganic sol-gel polymerization process).

In the present invention the term "in situ polymerization" refers to the sol-gel polymerization process of a precursor forming an inorganic polymer at the oil-water interphase of the emulsion as a result of the hydrolysis and condensation reactions of the precursor.

In the present invention, the term "active ingredient" refers to any molecule or substance that can be used in agriculture, industry (including food industry), medicine, cosmetics, and which grants the final product (cosmetics, pesticide, drug, etc.) at least one desired property.

In the present invention, the term "topical application" refers to an application on the skin, hair, ears, mucous membranes, rectal application, nasal application, as well as dental application within the oral cavity.

In the present invention, the term "TEOS" refers to tetraethoxysilane, which is a precursor of silica.

In the present invention, the term "loading" refers to the weight percentage of the active ingredient based on the total weight of the microcapsule defined by (w/w).

In the present invention, the term "loading of an active ingredient above 95%" refers to a weight percentage of the active ingredient above 95% (w/w) based on the total weight of the microcapsule. As the microcapsules constitute a population with different loading, this term refers to an average value of all measured microcapsules.

In the present invention, the term "concentration of the core material above 95%" refers to a weight percentage of the core material (including both the active ingredient and the excipients such as the liquid carrier) above 95% (w/w) based on the total weight of the microcapsules. As the microcapsules constitute a population with different concentrations of a core material, this term refers to an average value of all measured microcapsules.

SUMMARY OF THE INVENTION

According to one aspect of the present invention there is provided microcapsules having a core material encapsulated within a microcapsular shell, said core material comprises at least one active ingredient, wherein the microcapsular shell comprises at least one inorganic polymer comprising polymerized precursors obtained by in-situ polymerization of said precursors; wherein the concentration of the core material based total weight of the microcapsules is above 95% w/w.

According to another aspect of the present invention there is provided a composition comprising a carrier and microcapsules having a core material encapsulated within a microcapsular shell, said core material comprises at least one active ingredient, wherein the microcapsular shell comprises at least one inorganic polymer comprising polymerized precursors obtained by in-situ polymerization of said precursors; wherein the concentration of the core material based total weight of the microcapsules is above 95% w/w.

According to yet another aspect of the present invention there is provided a suspension, substantially free of colloidal silica, comprising microcapsules having a core material encapsulated within a microcapsular shell, said core material comprises at least one active ingredient, wherein the microcapsular shell comprises at least one inorganic polymer comprising polymerized precursors obtained by in-situ polymerization of said precursors; wherein the concentration of the core material based total weight of the microcapsules is above 95% w/w.

According to an additional aspect of the present invention there is provided a process for preparing microcapsules having a core material encapsulated within a microcapsular shell, said core material comprises at least one active ingredient, said process comprising the step of;
 preparing an oil-in-water emulsion by emulsification of an oily phase, comprising a water insoluble precursor and the core material, in an aqueous phase, comprising an aqueous solution having a pH in the range 2-7, under appropriate shear forces and temperature conditions;
 the process comprising at least one of the following conditions:
  (i) the concentration of the oily phase based on the total weight of the emulsion is from 50% to 90% w/w;
  (ii) the weight ratio of the precursors to the core material is from 5/95 to 25/75;
 thereby obtaining microcapsules having above 95% w/w of said core material.

DETAILED DESCRIPTION OF THE INVENTION

The present invention relates to microcapsules having a core material encapsulated within a microcapsular shell, said core material comprises at least one active ingredient, wherein the microcapsular shell comprises at least one inorganic polymer comprising polymerized precursors obtained by in-situ polymerization of said precursors; wherein the concentration of the core material based total weight of the microcapsules is above 95% w/w.

Preferably the concentration of the core material based total weight of the microcapsules is from 95% to 99% (w/w), more preferably the concentration of the core material based total weight of the microcapsules is from 95% to 98% (w/w). Preferably the concentration of the core material based total weight of the microcapsules is in the range 96%-99% (w/w), and more preferably in the range 96%-98%(w/w).

Preferably the core consists essentially of at least one active ingredient.

As used herein the term "consists essentially of at least one active ingredient" means that the core material comprises a high percentage (w/w) of an active ingredient and low percentage of excipients (such as the liquid carrier). Preferably the concentration of the active ingredient based on the total weight of the core is above 80% w/w, more preferably above 90% w/w and most preferably above 95% w/w. The term "consists essentially of an active ingredient" also mean that the core material may also include excipients which are needed for the preparation of the microcapsules or to dissolve the active ingredient. Preferably the concentration of the excipients based on the total weight of the core is up to 20% w/w, more preferably up to 10% w/w and most preferably up to 5% w/w.

Preferably the core material is said at least one active ingredient (i.e. does not include excipients such as a liquid carrier).

Where the active ingredient is an oil such as a sunscreen agent and additional excipients such as solvents or co-solvents are not needed in order to prepare the oily phase of the emulsion described in the process below, in this case the core material of the formed microcapsules is the active ingredient.

In other application, for example when the active ingredient is a dye it will be advantages to dissolve the active ingredient (dye) in a solvent at a concentration of a dye which is sufficient to grant the desired color property. In this case the core material comprises an excipient preferably an oily solvent and the active ingredient (dye).

Preferably the concentration of the dye in the core material is less than 1% w/w more preferably 0.0001%-0.1% w/w and most preferably 0.0001%-0.01% w/w. The concentration depends on the type of dye and its solubility.

Preferably the core is a liquid core and more preferably the liquid core is an oily core.

Preferably the liquid core is a solution, suspension or dispersion.

More preferably the liquid core is an oily core for example in the form of a solution, suspension or dispersion.

The active ingredient may be present in a dissolved, dispersed or suspended form in the core.

The microcapsules may be useful for cosmetic or medical applications. The microcapsules may also be used in agricultural, polymeric or food industry.

The microcapsules may be useful for any application wherein the active ingredient should be isolated, temporally or permanently from the ambient surroundings.

The active ingredient may be any molecules or substances that are soluble or that can be suspended in the precursor (metal or the semi metal alkoxides) of choice.

The active ingredient may be for example sunscreen agents, dental agents, fragrances, perfume, colors and dyes, food colors and food additives, waxes, antioxidants, humidifiers, vitamins, explosives, pesticides, biological molecules (such as enzymes, co-enzymes or antibodies), drugs, catalysts, reagents or mixtures thereof.

The drugs may be for example dermatological agents, anti-inflammatory agents, analgesics, anti-fungal agents, anti-biotics, anti-viral agents, anti-acne agents, anti histamines, skin whitening agents, anti-parasitic agents, muscle relaxants, steroids, hormones, astringents or mixtures thereof.

The active ingredient may be for example pesticides such as insecticides, herbicides or fungicides used in agriculture or industry.

Most preferably the active ingredient is a sunscreen agent.

The sunscreen agent may be for example a UVA absorber, a UVB absorber, or mixtures thereof.

The UVA absorber may be for example octylmethoxy cinnamate, p-aminobenzoic acid, or mixtures thereof.

The UVB absorber may be for example 3-butylmethoxydibenzoyl methane, benzophenone-3 or mixtures thereof.

The sunscreen agent (ultra-violet absorbing molecules or ultra-violet reflecting substances) may be for example octylmethoxy cinnamate, 3-butylmethoxydibenzoyl methane, benzophenone-3, benzophenone-1, benzophenone-2, benzophenone-6, benzophenone-4, benzophenone-8,2-ethylhexyl p-methoxycinnamate, p-aminobenzoic acid, 2-ethylhexyl N,N-dimethyl-p-aminobenzoate, 2-cyano-3,3-diphenylacrylic acid 2-ethylhexyl ester, 2-ethylhexyl-2-cyano-3,3-diphenylacrylate, oxybenzone, 2-phenylbenzimidizole-5-sulfonic acid, homomenthyl salicylate, octyl salycilate, 4,4'-methoxy-t-butyldibenzoylmethane, 4-isopropyl dibenzoylmethane, 3-(4-methylbenzyledene) camphor, 3-benzylidene camphor, triethanolamine salicylate, 4-N,N-(2-ethylhexyl)methyl aminobenzoic acid ester of 2,4-dihydroxybenzophenone, 4-N,N-(2-ethylhexyl) methyl aminobenzoic acid ester of 4-hydroxydibenzoylmethane, 4-N,N-(2-ethylhexyl)methyl-aminobenzoic acid ester of 2-hydroxy-4-(2-hydroxyethoxy)-benzophenone, 4-N,N-(2-ethylhexyl)methyl aminobenzoic acid ester of 4-(2-hydroxyethoxy)dibenzoylmethane, or mixtures thereof.

Most preferably the sunscreen agent is selected from octylmethoxy cinnamate, 3-butylmethoxydibenzoyl methane, benzophenone-3,2-ethylhexyl-2-cyano-3,3-diphenylacrylate, and mixtures thereof.

Additional sunscreen agents which may be used in the present invention are disclosed in U.S. Pat. Nos. 6,238,650, 6,468,509, 6,303,149, U.S. Pat. No. 6,436,375 and International publication WO 03/039510. The disclosures of these patents and publications are incorporated herein by reference in their entirety.

The active ingredient may be for example natural food colors or synthetic food colors or food additives used in food products or oral drugs.

The active ingredient may be for example natural food colors or synthetic food colors used in cosmetic colors and skin applications.

Preferably the active ingredient is a dye.

The active ingredient may be for example a dye such as a fluorescent dye.

The fluorescent dye may be used in cosmetics, pharmaceutics, inks or any other industries where it is necessary to avoid the contact of the dye with its dispersing environment or with the different organs of the human body (such as the skin).

The fluorescent dye may be for example nile red, perylene, pyrene, anthracene, or mixtures thereof.

Preferably the precursors are selected from metal alkoxide monomers, semi-metal alkoxide monomers, metal ester monomers, semi-metal ester monomers and from monomers of the formula $M(R)_n(P)_m$, wherein M is a metallic or semi metallic element, R is a hydrolysable substituent, n is an integer from 2 to 6, P is a non polymerizable substituent and m is an integer from 0 to 6, a partially hydrolyzed and partially condensed polymer thereof, or any mixture thereof.

Preferably the metallic or semi metallic element is selected from Si, Ti, Zr, Al, and Zn.

The precursor may be a single monomeric unit or alternatively the precursor may be comprised of a number of monomeric units (at times also referred to as "prepolymer").

For example, the precursor may be an oligomer of the precursor for example, a prehydrolyzed tetraethoxy silane (TEOS) which is based on the hydrolysis of TEOS, which may be used in order to obtain short chain polymers (prepolymer) that can also be used for encapsulation.

In a preferred embodiment of this invention, the precursors are selected from silicon alkoxide monomers, silicon ester monomers, monomers of the formula $Si(R)_n(P)_m$, where R is a hydrolysable substituent, n is an integer from 2 to 4, P is a non polymerizable substituent and m is an integer from 0 to 4, a partially hydrolyzed and partially condensed polymer thereof, and any mixture thereof.

In another preferred embodiment of this invention, several precursors are used together in the oil phase as a mixture of several metals or semi metal monomers, to afford a microcapsule shell which is a composite including different metal and/or semi metal elements in the final product.

Preferably the precursor is selected from metal alkoxide monomer, semi metal alkoxide monomer, a partially hydrolyzed and partially condensed polymers thereof, and any mixture thereof.

Preferably the semi metal alkoxide monomer is silicon alkoxide monomer.

Preferably the silicon alkoxide monomer is selected from tetramethoxy silane (TMOS), tetraethoxy silane (TEOS), and mixtures thereof.

Most preferably the silicon alkoxide monomer is tetraethoxy silane.

Preferably the active ingredient is a sunscreen agent and said precursor is tetraethoxy silane.

The sunscreen agent may be as defined above.

Most preferably the sunscreen agent is selected from octylmethoxy cinnamate, 3-butylmethoxydibenzoyl methane, benzophenone-3,2-ethylhexyl-2-cyano-3,3-diphenylacrylate, or mixtures thereof and said precursor is tetraethoxy silane.

The precursors which may be used in the present invention (termed also sol-gel precursers) are also described in U.S. Pat. Nos. 6,303,149, 6,238,650, 6,468,509, 6,436,375 and International publication Nos. WO 01/80823, WO 03/034979 and WO 03/039510 (the disclosures of these patents and publications are incorporated herein by reference in their entirety).

Recognizing that metal and semi metal alkoxide monomers (and their partially hydrolyzed and condensed polymers) such as tetramethoxy silane (TMOS), tetraethoxy silane (TEOS),) etc. are very good solvents for numerous molecules and substances (active ingredients) is highly advantageous since it facilitated the utilization of this solubility property to load the dissolved molecules or substances in the monomeric precursor solvent or in the hydrolysis-condensation polymer of the monomer solvent. Nonetheless, the present invention may also be used to coat or load molecules or substances (active ingredients) which can be suspended in the precursors.

The particle size of the microcapsules may be in the range of 0.01-1000 μm in diameter, preferably 0.1-100 μm in diameter and more preferably 1-10 μm in diameter.

The microcapsules of the present invention may be useful for human or non-human applications, as they may be easily incorporated in various carriers. The microcapsules may be easily dispersed or suspended in a carrier or diluent.

Simple mixing with any suitable mixer or stirrer is sufficient to achieve an effective dispersion. If necessary high shear forces may be applied to facilitate fast and efficient mixing of the microcapsules in the carrier.

Preferably the microcapsules are non-leaching when dispersed in a carrier.

The present invention additionally relates to a composition comprising microcapsules as defined in the present invention and a carrier.

The composition may be for example a cosmetic composition, a pharmaceutical composition, a food composition, a composition used in agriculture or industrial processes.

Preferably the microcapsules are dispersed in the carrier.

The carrier may be a cosmetic carrier, a pharmaceutical carrier, a food carrier, a carrier used in agriculture or industrial processes.

The carrier may be a liquid, a semi solid or a solid carrier.

The carrier may be for example an emulsion, a cream, an aqueous solution, an oil, an ointment, a paste, a gel, a lotion, a milk, a suspension, a powder, a processed food, a spray, a paint, a lacquer, a coating, a plastic or a detergent.

The carrier may further comprise at least one non-encapsulated active ingredient.

The final form of the composition may be for example an emulsion, an aqueous solution, an oil, a semi-solid formulation (such as a cream, an ointment, a paste, or a gel), a lotion, a milk, a suspension, a powder, a capsule, an aerosol, a spray, a foam, a shampoo, a hair conditioner, a lacquer, a makeup, a solid stick, a toothpaste, a food, a paint, a plastic or a coating.

The particle size of the microcapsules can be controlled to the range 0.01-1000 μm, preferably 0.1-100 μm, more preferably 1-10 μm in diameter.

The particle size of the microcapsules can be controlled for example by controlling the particle size of the oil droplets of the emulsion used to prepare the microcapsules (the preparation of the emulsion and microcapsules is detailed below in the described process).

The composition may be in the form of a suspension or a powder wherein the powder particles (microcapsules) or the suspended particles (microcapsules) are preferably of 0.01-1000μ in diameter.

More preferably the composition may be in the form of a suspension or a powder wherein the powder or the suspension includes 0.1-10μ (diameter) spherical particles (microcapsules), has a smooth texture, and is transparent when suspended in cosmetic or skin care formulations and applied to skin.

The compositions of the present invention may be applied topically.

By one embodiment the microcapsules of the present invention are leachless (non-leaching), this is highly advantageous since encapsulation of a sensitive active ingredient in the microcapsules can protect it from other ingredients in the formulation and from the environment, and thus extends the shelf life of the end-product. The active ingredients in sunscreens have been reported to cause contact dermatitis and may cause photo contact dermatitis. Moreover, the light-excited species of these reagents may undergo photodecomposition reactions resulting in the production of free radicals and reactive oxygen species, which may bear deleterious effects on live tissues. Therefore, formulating leachless microcapsules is particularly advantageous in sunscreen compositions where there is a need to isolate the sunscreen active agents an/or their possible photodecomposition products from the live tissues.

Additional examples and applications in which isolation of the active ingredients from the environment is advantageous are described in the background of the invention.

Surprisingly it was found in the present invention, in accordance to the leachless aspect, that the leaching of the microcapsules loaded with an active ingredient, being the sunscreen agent, into cosmetic oils or into an aqueous solution including a surfactant is less than 1%, preferably less than 0.5% after vigorous shaking.

By another embodiment the microcapsules of the present invention are designed to release the active ingredient.

In certain applications such as medical (oral or topical) or agricultural it may be desired to achieve immediate or controlled release of the active ingredient from the microcapsules.

The release of active ingredient from the microcapsule can be designed to be immediate, delayed or sustained; this can be controlled by varying the composition of the microcapsular shell, its diameter, and by varying the composition of the carrier surrounding the microcapsules.

Release can be obtained and controlled by aging time, thermal treatment or any mechanical mean that can change the characteristic porosity or strength of the shell, or by chemical means such as organic polymers and/or surfactants that may be added while the microcapsules are being formed, to control the surface nature of the shell and the rate of diffusion through the pores. Since the microcapsular shell may be composed of sub-micron particles, the effective pore size of the shell may be controlled by electrolytes or any other chemical component of the formulation. This may be a trigger for release of the active ingredients from the microcapsules.

Since the encapsulation creates micro-domains within the entire formulation, one active ingredient can be encapsulated while a second active ingredient can be present in the carrier that surrounds the microcapsules. This is advantageous when the ingredients acts synergistically together, yet one is chemically reactive with another.

Alternatively each of the active ingredients may be microencapsulated in separate microcapsules.

In an alternative, the active ingredient may be encapsulated alone, or with other ingredients within the same microcapsule. Co-encapsulation of compounds that enhance stability of the sensitive ingredient is beneficial. For example, anti oxidants can be co-encapsulated with oxygen-sensitive or oxidant-sensitive ingredients, to give "localized protection".

The present invention additionally relates to a suspension, substantially free of colloidal silica, comprising microcapsules as described in the present invention.

The colloidal silica (nanoparticles of silica) is produced during the polymerization of the precursors at the oil-water interphase as an intermediate of the production of the final microcapsules shell. The monomer precursors used in the polymerization reaction do not remain as such but either constitute the microcapsules shell or are left as residual material in the form of colloidal silica unattached to the shell. Preferably 0-20% w/w, more preferably 0-10% w/w and most preferably 0-5% of the colloidal silica is unattached to the shell of the microcapsules (i.e. present in the reaction medium in a free form and does not constitute the microcapsule's shell).

As used herein the term "substantially free of colloidal silica" means that the suspension of the microcapsules include minute, insignificant amount of the colloidal silica in the suspension medium, preferably less than 20% w/w more preferably less than 10% and most preferably less than 5% w/w.

The term "minute insignificant amount of the colloidal silica in the suspension medium" means that preferably 0-20% w/w, more preferably 0-10% w/w and most preferably 0-5% w/w of the colloidal silica is unattached to the shell of the microcapsules (i.e. present in the reaction medium in a free form and does not constitute the microcapsule's shell).

The term "suspension medium" refers to the reaction medium used to prepare the microcapsules and more particularly to the aqueous phase used in the preparation of the emulsion and microcapsules as will be described in the process below.

Similarly, depending on the type of the precursor used to prepare the microcapsules it is appreciated that the suspension is also substantially free of colloidal Titania, Zirconia, Alumina, etc.

Preferably the suspension consists essentially of the microcapsules.

As used herein the term "suspension consists essentially of the microcapsules" means that the suspension is substantially free of or contains an acceptable concentration of by-products (such as free colloidal silica) produced during the preparation of the microcapsules, which enables using the suspension without further purification.

Most preferably the suspension of microcapsules which is obtained by the process described in the present invention is used without the need of further purification steps.

The suspension may be dispersed in a carrier.

The carrier may be a cosmetic carrier, a pharmaceutical carrier, a food carrier, a carrier used in agriculture or industrial processes.

The carrier may be a liquid, a semi solid or a solid carrier.

Preferably the microcapsules are non-leaching in the medium of the suspension.

Preferably the suspension is non-leaching when the suspension is dispersed in a carrier.

The present invention further relates to a process for preparing microcapsules having a core material encapsulated within a microcapsular shell, said core material comprises at least one active ingredient, said process comprising the step of;
preparing an oil-in-water emulsion by emulsification of an oily phase, comprising a water insoluble precursor and the core material, in an aqueous phase, comprising an aqueous solution having a pH in the range 2-7, under appropriate shear forces and temperature conditions;
the process comprising at least one of the following conditions:
(i) the concentration of the oily phase based on the total weight of the emulsion is from 50% to 90% w/w;
(ii) the weight ratio of the precursors to the core material is from 5/95 to 25/75;
thereby obtaining microcapsules having above 95% w/w of said core material.

Preferably the process comprising a combination of the two conditions (i) and (ii).

Preferably the process comprising condition (ii).

The process of the present invention is based on the preparation of an oil-in-water emulsion by emulsifying a hydrophobic solution (oily phase) that comprises the precursors and the core material comprising the at least one active ingredient (molecules or substances to be loaded), in aqueous solution, with or without the need for mixing said emulsion with another aqueous solution to accelerate the condensation-polymerization reaction.

In the present invention the term "mixing" also relates to dropwise addition of one solution to the other, by pouring one solution to the other, or any other method of combining the two solutions together.

Surprisingly it was found in the present invention that decreasing the weight ratio of the precursor to the core material to the range of 5/95-25/75, and/or preparing a concentrated oil-in water emulsion wherein the concentration of the oily phase in the emulsion is above 50% (w/w), and performing the condensation-polymerization process in a pH of 2-7, preferably 2-5, and more preferably 3-4, enables an efficient encapsulation of the core material with high concentration (above 95% w/w) of the core material and yet prevents the leaching of the core material (including the active ingredient) from the microcapsules. As the concentration of the oil phase in the emulsion increases the yield of the reaction increases because it is possible to obtain more microcapsules at each reaction.

Unexpectedly it was found that although the weight ratio of the precursor to the core material was decreased from the prior art typical data of about 50/50 to the range of 5/95-25/75, the polymerization of the precursor was of high efficiency and a higher yield was obtained from the point of view of the quantity of silica developed on the shell of the microcapsule, as revealed by the high concentration of the core material and insignificant amount of the residual precursor in the reaction aqueous medium (in the form of colloidal silica) in which the microcapsules are produced. This is highly advantageous since it minimizes the environmental contamination, does not require treatment of the reaction waste water and thus simplifies and lowers the cost of the process.

Another advantage of the process of the present invention is the elimination of the step of isolation of the microcapsules by centrifugation, filtration, re-suspension etc, which is needed in the prior art in order to obtain a high concentration of particles in the final product (in previous patent we needed to isolate the microcapsules from the mother liquor in order to obtain a concentration of 40% (by weight) of sunscreen in the suspension while in the present invention we obtain it at the and of the reaction due to the high loading of the active ingredient in the oil phase at the emulsion step and due to the high concentration of the oily phase in the emulsion—50-90% w/w.

The process may further comprise the step of mixing (diluting) and stirring said emulsion with another aqueous solution at a suitably selected pH in the range 2-7, to obtain loaded microcapsules in a suspension.

Preferably the pH of the aqueous solution is in the range 2-5. More preferably the pH of the aqueous solution is in the range 3-4.

The pH ranges above refer to the aqueous solution of the emulsification step and/or the optional further step of mixing and stirring the emulsion with another aqueous solution.

In case the aqueous phase of the emulsion has a pH in the range 2-5, more preferably 3-4, the microcapsules in suspension can be obtained after the emulsification step without the need of further steps such as mixing and stirring the obtained emulsion with another aqueous solution as described above or adding a catalyst such as an acidic solution.

Preferably the microcapsules in suspension are obtained after the emulsification step without the need of further steps such as mixing and stirring the obtained emulsion with another aqueous solution as described above or adding a catalyst such as an acidic solution. In this case the pH of the aqueous solution is preferably in the range 2-5 and more preferably in the range 3-4.

This case (where the microcapsules in suspension are obtained after the emulsification step without the need of further steps) is preferred since the yield of the production of the microcapsules per reaction is higher compared to a process comprising a further step of adding another solution to obtain the microcapsules. Occasionally it will be beneficial to further mix and stir the obtained emulsion with another aqueous solution to avoid the interconnection between the microcapsules obtained by the first process (i.e. without the addition of another aqueous solution).

Performing the condensation-polymerization process in a pH range of 2-7, preferably in the range of 2-5, and more preferably in the range of 3-4 was found to be highly advantageous since at this catalytic pH a more linear polycondensation reaction is obtained at the oil-water interface of the emulsion, thereby reducing the risk of coalescence between the oil drops which can take place at a higher pH. At a higher pH (above pH 7) a random fast polycondensation reaction produces lots of oligomers which promotes the interconnection of the dispersed oil drops.

The emulsification in the process of the present invention may be conducted by adding an aqueous phase to an oily phase or alternatively by adding an oily phase to an aqueous phase.

Preferably the process comprising:
(a) mixing a core material and a precursor forming an oily phase;
(b) emulsifying said oily phase in an aqueous phase having a pH in the range 2-7 to form an oil-in water emulsion; and
(c) stirring the product obtained in step (b) until microcapsules are formed.

Preferably the process comprising:
(a) mixing a core material and a precursor in a production reactor forming an oily phase;
(b) adding an aqueous phase having a pH in the range 2-7 to the production reactor in step (a) to form an oil-in-water emulsion; and
(c) stirring the product obtained in step (b) until microcapsules are formed.

Preferably the processes of the present invention are conducted in one production reactor.

Conducting the process in one reaction production is preferred since it reduces handling and the cost of the process.

In a preferred embodiment all the ingredients are mixed in one reactor without transferring the product obtained at the end of each stage of the encapsulation (such as the oily phase, aqueous phase or the emulsion) to a new reactor for further handling of the product until it is ready for special treatment such as isolation of the microcapsules by centrifugation.

The above described process provides also a new process for making emulsions in which all ingredients are added to one production reactor. The novelty of preparing the emulsion and the obtained microcapsules is also based on the order at which the chemical reagents (ingredients) are added to the reactor. The process described is highly advantageous because it is simplified in production, highly efficient, saves time, and therefore lower in cost, compared to the "classical" procedure, in which each phase (oil and water) are prepared separately in two different reactors and then mixed in a third reactor or mixed in the water phase reactor after addition of the oil phase to the water phase or mixed in the oily phase reactor after addition of the water phase to the oily phase (depending on the type of emulsion (w/o or o/w) and the type of surfactant. Classically the dispersed phase is added to the dispersing phase but it is also possible to add inversely if the surfactant used for emulsification do not have the ability to produce the opposite type of emulsion).

The emulsification in the present invention may also be conducted by the "classical" procedure, in which each phase (oil and water) are prepared separately in two different reactors and then mixed in a third reactor or by preparing each phase (oil and water) separately in two different reactors and then adding the oily phase to the aqueous phase (or adding the water phase to the oily phase) as described above.

Most preferably, the emulsification and production of the microcapsules is conducted in one reactor as detailed above.

Preferably the stirring in step (c) is conducted for at least 12 hours. Preferably the aqueous phase in step (b) includes a surfactant.

Preferably the process further comprising adding a catalyst after step (b). Preferably the process further comprising the step of adding an ingredient selected from a surfactant, a catalyst and a mixture thereof after step (b).

The process may further comprise the step of diluting with an aqueous diluent after adding said ingredient.

Preferably the aqueous diluent is water.

Preferably the surfactant is selected from a cationic surfactant, an anionic surfactant, a non-ionic surfactant and mixtures thereof.

Preferably the surfactant is a cationic surfactant.

Most preferably the cationic surfactant is cetyltrimethyl ammonium chloride.

Preferably the catalyst is an acidic solution.

Preferably the acidic solution is an hydrochloric acid solution.

Preferably the pH of the aqueous phase is above 5 and said catalyst is added to provide a pH in the range of 2-5.

Preferably the pH of the aqueous phase is above 4 and said catalyst is added to provide a pH in the range of 3-4.

The hydrophobic oily phase and/or the aqueous solution may include additional surfactants or any additives to improve the product.

The surfactant may be for example an anionic surfactant, a cationic surfactant, a non-ionic surfactant, an anionic polymeric surfactant, a cationic polymeric surfactant, a non-ionic polymeric surfactant, or mixtures thereof.

The emulsification is performed using at least one emulsification agent (surfactant).

The aqueous solution may comprise at least one hydrophilic (water soluble) surfactant.

The oily phase may comprise at least one hydrophobic surfactant.

The oily phase may comprise at least one hydrophobic polymeric surfactant.

Preferably hydrophobic surfactant or hydrophobic polymeric surfactant is a non-ionic surfactant.

The hydrophilic surfactant may be for example an anionic, a cationic, an non-ionic surfactant or mixtures thereof.

The emulsification is preferably performed using at least one hydrophilic surfactant.

Preferably the hydrophilic surfactant is a cationic surfactant.

Most preferably the cationic surfactant is cetyltrimethyl ammonium chloride.

Additional surfactants which may be used in the present invention are described in: Cationic Surfactants, edited by Eric Jungermann from the series Surfactant Science series volume 4, see also volumes 34, 37, 53 of the same series, incorporated herein by reference in their entirety; and Remington's Pharmaceutical Sciences, $16^{th}$ ed., Mack Publishing Company, Easton, Pa. (1980), incorporated herein by reference in its entirety.

The concentration of the cationic surfactant in the aqueous solution (aqueous phase) may be from 0.1 to 5% (w/w) and most preferably from 0.5 to 1.5 (w/w).

Surprisingly it was found in the present invention that the cationic surfactant, cetyltrimethyl ammoniumchloride, used as a single emulsifying agent at low concentrations is capable of emulsifying a concentrated oil-in-water emulsion comprising above 50% w/w of the oily phase based on the total weight of the emulsion. The emulsion formed was found to be stable for at least 3-4 hours at room temperature.

The process of the present invention may further comprise an additional step of isolating and rinsing the microcapsules through cycles selected from separation by centrifuge or by filtration and re-suspension in water, evaporation and re-suspension in water or by dialysis or by any other conventional means known in the art.

The process of the present invention may further comprise the step of isolating and rinsing the microcapsules through procedures selected from at least one of: separation by centrifuge; filtration; evaporation; re-suspension in an aqueous medium; and dialysis.

The aqueous medium is preferably water.

The suspension so obtained may be stabilized by adding additives such as non-ionic, cationic or anionic polymers or surfactants or mixtures thereof.

The suspension may be stabilized by any other suitable suspending agent to obtain the final product in a suspension form.

The process may further comprise the step of removing the water to obtain the final product (microcapsules) in a powder form.

The water may be removed by any conventional means such as evaporation filtration etc.

The process may further comprise the step of adding-reconstitution additives such as non-ionic, cationic or anionic surfactants or polymers, or mixtures thereof. (The surfactants or polymers maybe non-ionic, cationic or anionic).

Preferably the emulsion is prepared at a temperature between 5-20° C. more preferably 10-18° C. In a subsequent step the reaction may be heated to a reaction temperature above 20° C. The pH of the emulsion may be between 2-7, more preferably between pH 2-5 and most preferably pH 3-4 in order to encourage the reaction to proceed at room temperature.

The emulsion obtained (with or without the additional step of diluting with another aqueous solution) may further comprise an additional step selected from: heating, cooling, subjecting to vacuum or pressure, keeping under inert gas atmosphere, subjecting to changes in pH and subjecting to an aging period preferably of up to 14 days.

In the present invention, the term "aging" refers to the period of time added over the end of the microcapsular shell (silica-shell) formation, needed in order to obtain the smallest leaching rate of the active due to closure of the open pores of the shell.

The concentration of the oily phase in the emulsion may be from 50% to 80% (w/w).

The concentration of the oily phase in the emulsion may be from 50% to 70% (w/w).

The concentration of the oily phase in the emulsion may be from 55% to 70% (w/w).

The concentration of the oily phase in the emulsion may be from 60% to 70% (w/w).

The concentration of the oily phase in the emulsion may be from 65% to 70% (w/w).

Preferably the weigh ratio of the precursors to the core material is from 5/95 to 20/80.

Preferably the weigh ratio of the precursors to the core material is from 5/95 to 15/85.

More preferably the weigh ratio of the precursors to the core material is from 10/90 to 15/85.

Most preferably the weigh ratio of the precursors to the core material is from 10/90 to 15/85 and the pH of said aqueous solution is 3-4.

Preferably the concentration of the core material based total weight of the microcapsules is from 95% to 99% (w/w).

More preferably the concentration of the core material based total weight of the microcapsules is from 95% to 98% (w/w). Preferably the concentration of the core material based total weight of the microcapsules is in the range 96%-99% (w/w), and more preferably in the range 96%-98%(w/w).

Preferably the core material consists essentially of said at least one active ingredient.

Preferably the core material is said at least one active ingredient.

Preferably the core is a liquid core.

Preferably the liquid core is an oily core.

Preferably the liquid core is a solution, suspension or dispersion.

More preferably the liquid core is an oily core for example in the form of a solution, suspension or dispersion.

The oily phase comprising the precursor and the core material (including the active ingredient) are preferably water immiscible.

The loaded active ingredient may be any molecule or substances that are soluble or that can be suspended in the precursor (metal or in the semi metal alkoxides) of choice.

Preferably the active ingredient is selected from sunscreen agents, dental agents, fragrances, perfume, colors and dyes, food colors, food additives, waxes, antioxidants, humidifiers, vitamins, explosives, pesticides, biological molecules, drugs, catalysts, reagents, and mixtures thereof.

The drug may be for example dermatological agents, anti-inflammatory agents, analgesics, anti-fungal agents, anti-biotics, anti-viral agents, anti-acne agents, anti histamines, skin whitening agents, anti-parasitic agents, muscle relaxants, steroids, hormones, astringents, and mixtures thereof.

The active ingredient may be for example pesticides such as insecticides, herbicides or fungicides used in agriculture or industry.

Most preferably the active ingredient is a sunscreen agent.

Preferably the sunscreen agent is selected from a UVA absorber, a UVB absorber, and mixtures thereof.

The UVA absorber may be for example octylmethoxy cinnamate, p-aminobenzoic acid, or mixtures thereof.

The UVB absorber may be for example 3-butylmethoxy-dibenzoyl methane, benzophenone-3, or mixtures thereof.

Preferably the sunscreen agent is selected from octylmethoxy cinnamate, 3-butylmethoxydibenzoyl methane, benzophenone-3, benzophenone-1, benzophenone-4, benzophenone-2, benzophenone-6 and benzophenone-8,2-ethylhexyl p-methoxycinnamate, p-aminobenzoic acid, 2-ethylhexyl N,N-dimethyl-p-aminobenzoate, 2-cyano-3,3-diphenylacrylic acid 2-ethylhexyl ester (octocrylene), 2-ethylhexyl-2-cyano-3,3-diphenylacrylate, oxybenzone, 2-phenylbenzimidizole-5-sulfonic acid, homomenthyl salicylate, octyl salycilate, 4,4'-methoxy-t-butyldibenzoylmethane, 4-isopropyl dibenzoylmethane, 3-(4-methylbenzyledene) camphor, 3-benzylidene camphor, triethanolamine salicylate, 4-N,N-(2-ethylhexyl)methyl aminobenzoic acid ester of 2,4-dihydroxybenzophenone, 4-N,N-(2-ethylhexyl) methyl aminobenzoic acid ester of 4-hydroxydibenzoyl-methane, 4-N,N-(2-ethylhexyl)methyl-aminobenzoic acid ester of 2-hydroxy-4-(2-hydroxyethoxy)-benzophenone, 4-N,N-(2-ethylhexyl)methyl aminobenzoic acid ester of 4-(2-hydroxyethoxy)dibenzoylmethane and mixtures thereof.

More preferably the sunscreen agent is selected from octyl-methoxy cinnamate, 3-butylmethoxydibenzoyl methane, benzophenone-3,2-ethylhexyl-2-cyano-3,3-diphenylacrylate, and mixtures thereof.

Preferably the active ingredient is a dye. The dye may be for example a fluorescent dye.

Preferably the fluorescent dye is selected from nile red, perylene, pyrene, anthracene, and mixtures thereof.

Preferably the precursors are selected from metal alkoxide monomers, semi-metal alkoxide monomers, metal ester monomers, semi-metal ester monomers and from monomers of the formula $M(R)_n(P)_m$, wherein M is a metallic or semi metallic element, R is a hydrolysable substituent, n is an integer from 2 to 6, P is a non polymerizable substituent and m is an integer from 0 to 6, a partially hydrolyzed and partially condensed polymer thereof, and any mixture thereof.

Preferably the metallic or semi metallic element is selected from Si, Ti, Zr, Al, and Zn.

The precursor may be a single monomeric unit or alternatively the precursor may be comprised of a number of monomeric units.

For example, the precursor may be an oligomer of the precursor for example, a prehydrolyzed tetraethoxy silane (TEOS) which is based on the hydrolysis of TEOS, which may be used in order to obtain short chain polymers that can also be used for encapsulation.

In a preferred embodiment of this invention, the precursors are selected from silicon alkoxide monomers, silicon ester monomers, monomers of the formula $Si(R)_n(P)_m$, where R is a hydrolysable substituent, n is an integer from 2 to 4, P is a non polymerizable substituent and m is an integer from 0 to 4, a partially hydrolyzed and partially condensed polymer thereof, and any mixture thereof.

In another preferred embodiment of this invention, several precursors are used together in the oil phase as a mixture of several metals or semi metal monomers, to afford a microcapsule shell which is a composite including different metal and/or semi metal elements in the final product.

Preferably the precursor is selected from metal alkoxide monomer, semi metal alkoxide monomer, a partially hydrolyzed and partially condensed polymers thereof, and any mixture thereof.

Preferably the semi metal alkoxide monomer is silicon alkoxide monomer.

Preferably the silicon alkoxide monomer is selected from tetramethoxy silane (TMOS), tetraethoxy silane (TEOS), and mixtures thereof.

Most preferably the silicon alkoxide monomer is tetraethoxy silane.

Preferably the active ingredient is a sunscreen agent and said precursor is tetraethoxy silane. The sunscreen agent may be as defined above.

Most preferably the sunscreen agent is selected from octyl-methoxy cinnamate, 3-butylmethoxydibenzoyl methane, benzophenone-3,2-ethylhexyl-2-cyano-3,3-diphenylacrylate, and mixtures thereof and said precursor is tetraethoxy silane.

The precursors which may be used in the present invention are also described in U.S. Pat. Nos. 6,303,149, 6,238,650, 6,468,509, 6,436,375 and International publication Nos. WO 01/80823, WO 03/034979 and WO 03/039510 (the disclosures of these patents and publications are incorporated herein by reference in their entirety).

Recognizing that metal and semi metal alkoxide monomers (and their partially hydrolyzed and condensed polymers) such as tetramethoxy silane (TMOS), tetraethoxy silane (TEOS) etc. are very good solvents for numerous molecules and substances (active ingredients) is highly advantageous since it facilitated the utilization of this solubility property to load the dissolved molecules or substances in the monomeric precursor solvent or in the hydrolysis-condensation polymer of the monomer solvent. Nonetheless, the present invention may also be used to coat or load molecules or substances (active ingredients) which can be suspended in the precursors.

Preferably the microcapsular shell formed comprises at least one inorganic polymer comprising polymerized precursors obtained by in-situ polymerization of the precursors.

The product obtained by the process may be in a powder form or a suspension form. Preferably the product obtained is a suspension of said microcapsules.

Preferably the product obtained is a powder of said microcapsules. When the product obtained is a powder of said microcapsules, the process includes a further step of removing the water by any means known in the art such as evaporation, filtration, freeze drying etc.

Preferably the product obtained by the process is a suspension of the microcapsules in the reaction medium of the process.

Preferably the suspension is substantially free of colloidal silica.

Preferably the particle size of the microcapsules is in the range of 0.01-1000 μm in diameter, more preferably in the range of 0.1-100 μm in diameter and most preferably in the range of 0.1-10 μm in diameter.

Preferably the microcapsules obtained by said process are non-leaching.

Preferably the term "non-leaching" refers to leaching of an active ingredient from the core of the microcapsules in an amount less than 5% w/w, more preferably less than 1% w/w more preferably less than 0.5% w/w more preferably less than 0.2% w/w and most preferably 0.1-0.2% w/w based on the total weight of the active ingredient in the core of the microcapsules. The above values refer to leaching into oils such as cosmetic oils or into surfactant containing aqueous solutions after vigorous shaking.

Preferably the leaching of the loaded active ingredient from the microcapsules into cosmetic oils or into surfactant-containing aqueous solution is less than 0.5%, preferably less than 0.2%, after vigorous shaking.

The product by process may accordingly vary for human or non-human applications, as the obtained aqueous suspension or the obtained dry powder may be easily incorporated in various carriers, such as creams and lotions, processed food, sprays, paints, lacquers, coatings, plastics and detergents.

The process may further comprise the step of dispersing the obtained microcapsules in a carrier.

The process of may further comprise the step of dispersing the obtained microcapsular suspension is a carrier without the need of purifying the suspension.

The carrier may be for example a cosmetic carrier, a pharmaceutical carrier, a food carrier, a carrier used in agriculture or industrial processes.

The carrier may be for example a liquid, a semi solid or a solid carrier.

Incorporation of the final product either in the form of a suspension or a powder in cosmetic formulations affords a transparent cream when applying to skin and has a smooth and pleasant contact.

Preferably the powder or suspension include spherical particles in the range of 0.1-10μ in diameter and has a smooth texture and is transparent when suspended in cosmetic or skin care formulations and when applied to the skin.

The process of the present invention may further include the step of modifying the surface charge of the products by adding anionic or cationic surfactants or polymers during any step of the process.

The process of the present invention may be conducted for example by the following non-limiting steps:

(a) A solution comprising of the water insoluble precursors (such as metal alkoxides) with or without a co-solvent and/or surfactant and the molecules to be encapsulated is emulsified in an aqueous solution having a pH in the range of 2-7, that may contain various surfactants, i.e. cationic, anionic or non-ionic surfactants, which are utilized to assist in stabilizing the emulsions. This emulsion is created under appropriate shear forces, utilizing an apparatus such as a homogenizer, a high-pressure homogenizer, a sonicator or membranes. The oil phase of the emulsion may optionally contain additives for improving the process and/or for obtaining an improved product. Examples for such additives are viscosity modifying reagents (i.e., thickeners), acids or bases that dissolve in the precursor of choice and assist in catalyzing the hydrolysis-condensation polymerization reaction, surfactants and others.

(b) The emulsion obtained by step (a) may be optionally mixed with another aqueous solution at a suitably selected pH (preferably a pH in the range of 2-7), which may also contain additional surfactants.

The emulsion obtained in step (a) and/or the reaction mixture of step (b) may be heated or cooled, subject to vacuum, or pressure, or kept under inert gas atmosphere, subject to changes in pH, or subject to an optional further aging period at room or accelerated temperature.

The resulting particles (microcapsules) can be optionally isolated and rinsed through cycles of centrifuge or filtration and re-suspension in deionized water or by dialysis or by any other technique known in the art.

The water insoluble solution (of step (a)) and the aqueous solutions (of steps (a) and (b) and of the optional further rinses) may contain various surfactants and any other additives for improving the process and/or the product.

Since the encapsulation process of the present invention is highly efficient, resulting in minute amounts of by products or reaction precursors in the aqueous reaction mixture, the obtained suspension of step (a) or (b) may be used without further treatment (such as rinsing, centrifugation, filtration, resuspension).

Occasionally, the reaction medium of the microcapsules may be changed for example by diafiltration, addition or replacement of the reaction medium.

The obtained suspension of step (a) or (b) may be incorporated for example into a suitable carrier.

The final product obtained by the process of the present invention may be used in a dispersion form without further treatment or after re-suspension in water with optional addition of suitable additives such as non-ionic, cationic or anionic polymers, or any other suspension aid known to the skilled artisan in this field. This dispersion shows extremely low leaching of the encapsulated material into surfactants solution in water, or into cosmetic oils.

The final product may also be used in a powder form, after removal of the water by appropriate means (such as drying, lyophilization, etc.) with optional addition of reconstitution additives such as non-ionic, cationic or anionic surfactants or polymers.

In case the core material is the active ingredient, the loading of the loaded active ingredient molecules or substances in the microcapsules is above 95% by weight of the solid (total weight of the microcapsule). The loading of the loaded molecules or substances (active ingredient) in the final aqueous dispersion may be up to 75% wt/wt more preferably 50-65% w/w and most preferably 60-65% w/w of the aqueous suspension.

Under appropriate choice of the reaction conditions the product is in the form of an aqueous suspension of up to about 75% w/w solids (microcapsules) more preferably 50-65% w/w and most preferably 60-65% w/w solids, consisting of sphere particles of 0.1-10 μm in diameter or in the form of fine free-flowing powder of sphere particles of 0.01-1000 μm in diameter.

By selecting the appropriate reaction conditions, the particle size of the final product can be controlled to be in the range from 0.01 to 1000μ in diameter and the leaching degree of the loaded molecule into cosmetic oils or into the surfactant-containing aqueous solution can be minimized.

The particle size (diameter) of the final product can be controlled to the range 0.01-1000μ, preferably 0.1-100μ, more preferably 0.1-10μ. The particles obtained by the present process can sustain high shear forces such as those present in a homogenizer or a sonicator without change in their encapsulation properties or in particle size distribution. The particles can also sustain increased temperatures up to 80° C. for 2 hours, γ-irradiation treatment up to 50 kGy without any such change.

In a preferred embodiment of the present invention, under appropriate choice of the reaction conditions, said product is in the form of a suspension comprising about 1 to 75% solids (microcapsules) more preferably 50-65% w/w and most preferably 60-65% w/w solids consisting of sphere particles of 0.1-10μ in diameter. Said suspension may be stabilized with the aid of suitable additives such as non-ionic, cationic or anionic polymers, or any other suspension aid known to the skilled artisan in this field. This suspension shows extremely low leaching of the encapsulated material into surfactants solution in water, or into cosmetic oils. Incorporation of this aqueous suspension in a cosmetic formulation affords a transparent cream when applying to skin and has a smooth and pleasant contact.

In another preferred embodiment of the present invention, under appropriate choice of the reaction conditions said product is in the form of a fine powder with a smooth and pleasant texture consisting of sphere particles of 0.1-10μ in diameter. Dispersion of this powder in a cosmetic formulation affords a transparent cream when applying to skin and has a smooth and pleasant contact.

The product by process may be designed to hold and/or isolate the encapsulated molecules or substances within the microcapsules.

The present invention further relates to an oil-in-water emulsion comprising:
  (a) an oily phase;
  (b) an aqueous phase; and
  (c) a surfactant
the emulsion is characterized in that the concentration of the oily phase in the emulsion is from 50% to 90% (w/w).

The concentration of the oily phase in the emulsion may be from 50% to 80% (w/w).

The concentration of the oily phase in the emulsion may be from 50% to 70% (w/w).

The concentration of the oily phase in the emulsion may be from 55% to 70% (w/w).

The concentration of the oily phase in the emulsion may be from 60% to 70% (w/w).

The concentration of the oily phase in the emulsion may be from 65% to 70% (w/w).

The surfactant may be an anionic surfactant, a cationic surfactant, a non-ionic surfactant or mixtures thereof.

Preferably the surfactant is a cationic surfactant.

Preferably the cationic surfactant is cetyltrimethyl ammonium chloride.

Additional surfactants which may be used in the present invention are described in: Cationic Surfactants, edited by Eric Jungermann from the series Surfactant Science series volume 4, see also volumes 34, 37, 53 of the same series, incorporated herein by reference in their entirety; and Remington's Pharmaceutical Sciences, $16^{th}$ ed., Mack Publishing Company, Easton, Pa. (1980), incorporated herein by reference in its entirety.

The concentration of the cationic surfactant in the aqueous phase maybe from 0.1 to 5% (w/w) and most preferably from 0.5 to 1.5% (w/w).

Preferably the oily phase comprises at least one active ingredient.

The active ingredient may be as described above.

The oily phase may comprise excipients such as a liquid (oily) carrier which is needed to dissolve or disperse the active ingredient.

Preferably the oily phase comprises at least one active ingredient and at least one precursor as described above.

The present invention additionally relates to a process for preparing an emulsion wherein the emulsion is prepared in one production reactor. The emulsion may be an oil-in-water or water-in-oil emulsion.

According to this method an oily phase, an aqueous phase, at least one surfactant and optionally additional additives are added and mixed in one production reactor to form an emulsion.

The oily phase, aqueous phase and surfactant may be as detailed above.

The process is highly advantageous since it is simplified in production, highly efficient, saves time, and therefore lower in cost, compared to the "classical" procedure, in which each phase (oil and water) are prepared separately in two different reactors and then mixed in a third reactor or mixed in the water phase reactor after addition of the oil phase to the water phase (or mixed in the oily phase reactor after addition of the water phase to the oily phase).

It should be understood that the invention is not limited in its application to the details of construction and the arrangement of the components set forth in the following description. The invention includes other embodiments and can be practiced or implemented in various ways. Also, it is to be understood that the phraseology and terminology employed herein is for the purpose of description only and should not be regarded as limiting.

EXAMPLES

The following examples clarify and demonstrate the present invention. They are not under any circumstances exclusive and do not intend to limit the scope of the present invention.

Background to Examples

As was mentioned in the background, the case of encapsulated sunscreen agents is of a special importance. Sunscreen products are widely used all over the world by all ages and gender, however, not only that the active ingredients in these products may cause contact dermatitis, but also the light-excited species of these reagents may cause photo contact dermatitis. Thus, encapsulating sunscreen active ingredients in transparent microcapsules like silica offers a sophisticated way to benefit from the light-absorbing capability of sunscreens, while substantially isolating them and/or their possible photodecomposition products from the live tissues.

Example 1

Octylmethoxy Cinnamate (OMC) in TEOS (Tetraethoxy Silane)

Octylmethoxy cinnamate (OMC), a widely used sunscreen has been encapsulated in microcapsules (silica microcapsules) by the following procedure:

276 g OMC was mixed with 24 g TEOS. The organic phase was emulsified in 161 g of aqueous solution containing 1% cetyltrimethyl ammonium chloride (CTAC) under high shear forces using a PT 6100 Polytron homogenizer at 9000 rpm for 5 minute. The vessel walls were cooled by immersion in an ice-water bath during the homogenizing process. This emulsion was then poured into an IKA LR-A 1000 Laboratory reactor, equipped with Eurostar Power control-visc P4 stirrer, containing 230.5 g of an aqueous solution having a pH of 3.8. The mixture was stirred at 400 rpm until the emulsion was completely mixed with the acidic solution, then the stirring rate was lowered to 60 rpm. The microcapsules obtained at the end of the reaction were isolated using a Sorvall RC-5C PLUS centrifuge equipped with SLA-1500 head at 12500 RPM for 30 min. The cake obtained by this process was reconstituted and stirred in pure water and further isolated by the same process. The cake obtained at the end of this process was reconstituted in an aqueous solution containing dispersants, preservatives and pH stabilizers: 1% w/v Polyvinylpirrolidone (dispersant), 0.3% w/v chlorophenesin (preservative), and 0.2 % w/v citric acid sodium citrate buffer (PH stabilizer).

The composition of the microcapsules obtained by this process consists of 97.55% (w/w) OMC, enveloped in a tiny silica shell having a particle size ranging between 0.75 and 2.5μ.

Formulation of the microcapsule suspension obtained by this process is described in Formula A, (Example 5, Table 1) which affords a transparent smooth and pleasant cream when applied on the skin Example 2

Benzophenone-3 (BP-3) and OMC in TEOS 82.8 g benzophenone-3, an UV-B as well as UV-A sunscreen agent, was dissolved in 193.2 g OMC. The obtained mixture was dissolved in 24 g TEOS and the organic phase was emulsified under high shear forces (same as described in Example 1) in 161 g aqueous solution containing 1% cetyltrimethyl ammonium chloride (CTAC). The obtained emulsion was then poured into the reactor (same as above) containing 230 g HCl aqueous solution at pH=3.5. The mixture was stirred at 400 rpm until the emulsion was completely mixed with the acidic solution, then the stirring rate was lowered to 60 rpm. The microcapsules obtain at the end of the reaction were isolated using a Sorvall RC-5C PLUS centrifuge equipped with SLA-1500 head at 12500 RPM for 30 min. The cake obtained by this process was reconstituted and stirred in pure water and further isolated by the same process. The cake obtained at the end of this process was reconstituted in an aqueous solution containing dispersants, preservatives and pH stabilizers: 1% w/v Polyvinylpirrolidone (dispersant), 0.3% w/v chlorophenesin (preservative), and 0.2% w/v citric acid sodium citrate buffer (PH stabilizer).

The composition of the microcapsules obtained by this process consists of 98.0% (w/w) BP-3/OMC solution, enveloped in a tiny silica shell having a particle size ranging between 0.75 and 2.5µ.

Formulation of this product in a neutral cosmetic cream (w/o lotion), afforded a cosmetic cream with a broad absorption spectrum in the UV, as expected from a mixture of those two sunscreens used. As a result a transparent smooth and pleasant feel cream was obtained when applied on the skin.

The content of the core (active ingredient) above 95% w/w, for the microcapsules tested was performed by the following method: 200 mg of the microcapsules suspension was dissolved in 1 ml of 5M NaOH (in order to dissolve the microcapsules shell) and then the mixture was diluted to a volume of 100 ml with methanol. The quantity of the active ingredient was determined by HPLC. The total weight of the solids (microcapsules) was determined by drying the suspension to maximum dryness at 105° C. The percentage of the active ingredient was determined by dividing the weight of the active ingredient by the total weight of the microcapsules.

Example 3

Butylnethoxydibenzoyl Methane (BMDBM) in 2-Ethylhexyl-2-cyano-3,3-diphenylacrylate (Octocrylene)

85.5 g BMDBM, a UVA sunscreen agent, was completely dissolved in 199.5 g octocrylene (UVB absorber) at 40 deg C. for 3 hours under intensive stirring. The obtained mixture was mixed with 15 g TEOS. The oil phase was then emulsified in 161 g of aqueous solution containing 1% (w/w) cetyltrimethyl ammonium chloride (CTAC) under high shear forces using a PT 6100 Polytron homogenizer at 15000 rpm for 10 minute. The vessel walls were cooled by immersion in an ice-water bath during the homogenizing process. This emulsion was then poured into an IKA LR-A 1000 Laboratory reactor, equipped with Eurostar Power control-visc P4 stirrer, containing 230.5 g HCl aqueous solution at pH 3.8. The mixture was stirred at 400 rpm until the emulsion was completely mixed with the acidic solution, then the stirring rate was lowered to 60 rpm. The microcapsules obtain at the end of the reaction were isolated using a Sorvall RC-5C PLUS centrifuge equipped with SLA-1500 head at 12500 RPM for 30 min. The cake obtained by this process was reconstituted and stirred in pure water and further isolated by the same process. The cake obtained at the end of this process was reconstituted in an 1% polyvinyl pyrrolidon (PVP K30, ISP) to afford a stable dispersion. The composition of the microcapsules obtained by this process consists of BMDBM/OCT solution enveloped in a tiny silica shell having a particle size of 0.3-2.7µ and an aqueous solution containing dispersants (1% w/v polyvinylpyrrolidin).

Formulation of this product in a neutral cosmetic cream (w/o lotion) afforded a cosmetic cream with a broad absorption spectrum in the UV, as expected from a mixture of those two sunscreens used. As a result a transparent smooth and pleasant feel cream was obtained when applied on the skin.

Example 4

Leaching-Out Test for the Encapsulated OMC in Water Suspension

In order to test the encapsulation properties of the microcapsules a leaching-out test was developed. The leaching out test was conducted by vigorous shaking of the suspension (of microcapsules) in 3% polyoxyethylene 20 sorbitan monostearate (Tween 60) solution in water at room temperature, followed by filtration of the particles (0.2µ cut off filter), and spectral analysis of the filtrate. The amount of the active ingredient leached (free active ingredient) was determined using a calibration curve. A linear response (calibration curve) of the active ingredient dissolved in the same surfactant solution (3% Tween 60 in water) determined spectrophotometrically was obtained at the concentration range 0-0.5% (w/w) of the active ingredient in the surfactant solution. This surfactant solution is commonly used in cosmetic formulations. The ability of this solution to solubilize encapsulated ingredients in water was confirmed by testing this procedure on encapsulated ingredients. The leaching out rate measured as described here for particles in suspension was less than 0.3%. The leaching was in the range 0.1-0.2 w/w.

No significant changes in the leaching rate under the same conditions was observed after homogenization of the suspension with an IKA product type disperser rotated at 20000 RPM for 35 min and after γ-irradiation treatment at 2.5 Mrad.

Example 5

In order to test the integrity of the encapsulation ability of the microcapsules after formulation in the cosmetic carrier described in table 1, a leaching-out test was developed. In this test the formulated particles are submitted to a vigorous shaking in a 3% polyoxyethylene 20 sorbitan monostearate (Tween 60) aqueous solution at room temperature followed by filtration of the particles (0.2µ cut off filter), and spectral analysis of the filtrate. The results show leaching out of 0.15% w/w of the active ingredient (OMC), which clearly show that the integrity of the encapsulation was saved.

TABLE 1

Formulation containing sunscreen-loaded particles obtained by the process of the present invention

| Formulation ingredients | % in formulation |
|---|---|
| water | 80.7 |
| Squalene | 5.0 |
| Glyceryl stearate & PEG-100 stearate | 5.0 |
| Cetyl alcohol | 2.0 |
| Methyl parabene | 0.1 |
| Propyl parabene | 0.1 |
| (*) Encapsulated OMC in final formulation | 7.0 |
| Leaching-out, %(w/w) | 0.15 |
| Leaching out rate, %/h (w/w) | 0.06 |

(*) From example 1

Example 6

Encapsulation of Fluorescent Dyes

The microencapsulation technology for the entrapment (microencapsulation) of fluorescent dyes is the same as the microencapsulation of oil soluble sunscreens with the modification that a non-liquid (solid powder) fluorescent dye is used.

The process for fluorescent dyes encapsulation was performed by the following steps:
 1. Dissolving of the fluorescent dye within a selected oil (active phase—AP);

2. Mixing the AP from (1) with TEOS which forms the oil phase (OP);
3. Emulsification of the OP from (2) with an aqueous surfactant solution (water phase) forming the emulsion stage (EM);
4. The EM obtained from (3) was diluted to a final concentration with a catalytic water solution (catalyst phase—CT) forming the reaction stage (RE) and mixed to form microcapsules.

The RE stage takes about 24 hs until the microcapsule's silica-shell is formed. After this period, depending on its final application, the product is kept in the reaction mixture or isolated by centrifugation or dried by any of the different drying technologies (lyophilization, spray-drying, freeze-drying).

The following microcapsules of fluorescent dyes were prepared by the described process:
1. Encapsulation of Nile Red (NR) dissolved in Isopropyl myristate (IPM)
2. Encapsulation of Nile Red (NR) dissolved in Homosalate (HMS)
3. Encapsulation of Nile Red (NR) dissolved in Dipropyleneglycoldibenzoate (DPGDB)
4. Encapsulation of Perylene (PE) dissolved in Octylmethoxycinnamate (OMC)
5. Encapsulation of Perylene (PE) dissolved in Homosalate (HMS)

Example 7

Encapsulation of Nile Red (NR) Dissolved in Isopropyl Myristate (IPM)

A solution of 387 gr of IPM containing 10 mg of NR was prepared and further mixed with 68 gr of Tetraethylorthosilicate (TEOS) in order to obtain the oil phase (OP). The OP was added to 246 gr of a 1% (w/w) water solution of cetyltrimethylammoniumchloride (CTAC) and mixed with a high-shear mixer. The emulsion obtained was mixed in a 1 liter reactor containing 350 gr of an acidic aqueous solution (containing 0.22 g of HCL) having a pH of 3.8 for 24 hours to form microcapsules in suspension.

Example 8

Encapsulation of Nile Red Dissolved in HMS, Nile Red Dissolved in DPGDB, Perylene Dissolved in OMC and Perylene Dissolved in HMS Microcapsules 2-5 listed above in example 6 were prepared as described above (in example 7) using instead of Nile Red (NR) dissolved in Isopropyl myristate (IPM) the following fluorescent dyes and oils:
2. Nile Red (NR) dissolved in Homosalate (HMS)
3. Nile Red (NR) dissolved in Dipropyleneglycoldibenzoate (DPGDB)
4. Perylene (PE) dissolved in Octylmethoxycinnamate (OMC); or
5. Perylene (PE) dissolved in Homosalate (HMS)

All the amounts of the ingredients used to prepare microcapsules 2-5 were identical to the amounts used in example 6.

Example 9

Octylmethoxy Cinnamate (OMC) in TEOS (Tetraethoxy Silane)

Octylmethoxy cinnamate (OMC), a widely used sunscreen is encapsulated in microcapsules (silica microcapsules) by the following procedure:

276 g OMC is mixed with 24 g TEOS. The organic phase is emulsified in 161 g of aqueous solution containing 1% cetyltrimethyl ammonium chloride (CTAC) having a pH of 3.5, under high shear forces using a PT 6100 Polytron homogenizer at 9000 rpm for 5 minute. The vessel walls are cooled by immersion in an ice-water bath during the homogenizing process. This emulsion is then poured into an IKA LR-A 1000 Laboratory reactor, equipped with Eurostar Power control-visc P4 stirrer and the mixture is stirred at 60 rpm for 24 hrs. The microcapsules obtain at the end of the reaction are isolated using a Sorvall RC-5C PLUS centrifuge equipped with SLA-1500 head at 12500 RPM for 30 min. The cake obtained by this process is reconstituted and stirred in pure water and further isolated by the same process. The cake obtained at the end of this process was reconstituted in an aqueous solution containing 1% w/v Polyvinylpirrolidone.

Alternatively the microcapsules in suspension obtained at the end of the reaction are used without the further steps of isolation and reconstitution. The microcapsules suspension obtained is easily dispersed in cosmetic carriers.

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. Microcapsules having a core material encapsulated within a microcapsular shell, said core material comprises at least one active ingredient,
wherein the microcapsular shell comprises at least one inorganic polymer comprising polymerized precursors obtained by in-situ polymerization of said precursors in a pH in the range of 2 to 7;
wherein the weight ratio of said precursors to said core material is in the range of 5/95 to 25/75 and wherein said precursors are selected from metal alkoxide monomers, semi-metal alkoxide monomers, metal ester monomers, semi-metal ester monomers and from monomers of the formula $M(R)_n(P)_m$, wherein M is a metallic or semi metallic element, R is a hydrolysable substituent, n is an integer from 2 to 6, P is a non polymerizable substituent and m is an integer from 0 to 6, a partially hydrolyzed and partially condensed polymer thereof, and any mixture thereof; and
wherein the concentration of the core material based on total weight of the microcapsules is 96% to 99% w/w.

2. The microcapsules of claim 1 wherein the active ingredient is selected from sunscreen agents, dental agents, fragrances, perfume, colors and dyes, food colors, food additives, waxes, antioxidants, humidifiers, vitamins, explosives, pesticides, biological molecules, drugs, catalysts, reagents, and mixtures thereof.

3. The microcapsules of claim 2 wherein said drug is selected from dermatological agents, anti-inflammatory agents, analgesics, anti-fungal agents, anti-biotics, anti-viral agents, anti-acne agents, anti histamines, skin whitening agents, anti-parasitic agents, muscle relaxants, steroids, hormones, astringents and mixtures thereof.

4. The microcapsules of claim 2 wherein said sunscreen agent is selected from octylmethoxy cinnamate, 3-butyl-methoxydibenzoyl methane, benzophenone-3, benzophenone-1, benzophenone-2, benzophenone-4, benzophenone-6, benzophenone-8,2-ethylhexyl p-methoxycinnamate, p-aminobenzoic acid, 2-ethylhexyl N,N-dimethyl-p-aminobenzoate, 2-cyano-3,3-diphenylacrylic acid 2-ethylhexyl ester, 2-ethylhexyl-2-cyano-3,3-diphenylacrylate, oxybenzone, 2-phenylbenzimidizole-5-sulfonic acid, homomethyl salicylate, octyl salicylate, 4,4'-methoxy-t-butyldibenzoyl-methane, 4-isopropyl dibenzoylmethane, 3-(4-methylbenzyledene) camphor, 3-benzylidene camphor, triethanolamine salicylate, 4-N,N-(2-ethylhexyl)methyl aminobenzoic acid ester of 2,4-dihydroxybenzophenone, 4-N,N-(2-ethylhexyl) methyl aminobenzoic acid ester of 4-hydroxydibenzoyl-methane, 4-N,N-(2-ethylhexyl)methyl-aminobenzoic acid ester of 2-hydroxy-4-(2-hydroxyethoxy)-benzophenone, 4-N,N-(2-ethylhexyl)methyl aminobenzoic acid ester of 4-(2-hydroxyethoxy)dibenzoylmethane, and mixtures thereof.

5. The microcapsules of claim 2 wherein said dye is a fluorescent dye.

6. The microcapsules of claim 1 wherein said precursors are selected from silicon alkoxide monomers, silicon ester monomers, monomers of the formula $Si(R)_n(P)_m$, where R is a hydrolysable substituent, n is an integer from 2 to 4, P is a non polymerizable substituent and m is an integer from 0 to 4, a partially hydrolyzed and partially condensed polymer thereof, and any mixture thereof.

7. The microcapsules of claim 6 wherein said silicon alkoxide monomer is selected from tetramethoxy silane, tetraethoxy silane, and mixtures thereof.

8. The microcapsules of claim 6 wherein said silicon alkoxide monomer is tetraethoxy silane.

9. The microcapsules of claim 1 wherein said active ingredient is a sunscreen agent and said precursor is tetraethoxy silane.

10. A composition comprising microcapsules having a core material encapsulated within a microcapsular shell, said core material comprises at least one active ingredient, wherein the microcapsular shell comprises at least one inorganic polymer comprising polymerized precursors obtained by in-situ polymerization of said precursors;
wherein the weight ratio of said precursors to said core material is in the range of 5/95 to 25/75 and wherein said precursors are selected from metal alkoxide monomers, semi-metal alkoxide monomers, metal ester monomers, semi-metal ester monomers and from monomers of the formula $M(R)_n(P)_m$, wherein M is a metallic or semi metallic element, R is a hydrolysable substituent, n is an integer from 2 to 6, P is a non polymerizable substituent and m is an integer from 0 to 6, a partially hydrolyzed and partially condensed polymer thereof, and any mixture thereof; and
wherein the concentration of the core material based total weight of the microcapsules is above 95% w/w; and a carrier.

11. A suspension, substantially free of colloidal silica, comprising microcapsules having a core material encapsulated within a microcapsular shell, said core material comprises at least one active ingredient,
wherein the microcapsular shell comprises at least one inorganic polymer comprising polymerized precursors obtained by in-situ polymerization of said precursors;
wherein the weight ratio of said precursors to said core material is in the range of 5/95 to 25/75 and wherein said precursors are selected from metal alkoxide monomers, semi-metal alkoxide monomers, metal ester monomers, semi-metal ester monomers and from monomers of the formula $M(R)_n(P)_m$, wherein M is a metallic or semi metallic element, is a hydrolysable substituent, n is an integer from 2 to 6, P is a non polymerizable substituent and m is an integer from 0 to 6, a partially hydrolyzed and partially condensed polymer thereof, and any mixture thereof; and
wherein the concentration of the core material based total weight of the microcapsules is 96% to 99% w/w.

12. A process for preparing microcapsules having a core material encapsulated within a microcapsular shell, said core material comprises at least one active ingredient,
said process comprising the step of;
preparing an oil-in-water emulsion by emulsification of an oily phase, comprising a water insoluble precursor and the core material, in an aqueous phase, comprising an aqueous solution having a pH in the range 2-7 and wherein said precursor is selected from metal alkoxide monomers, semi-metal alkoxide monomers, metal ester monomers, semi-metal ester monomers and from monomers of the formula $M(R)_n(P)_m$, wherein M is a metallic or semi metallic element, R is a hydrolysable substituent, n is an integer from 2 to 6, P is a non polymerizable substituent and m is an integer from 0 to 6, a partially hydrolyzed and partially condensed polymer thereof, and any mixture thereof, under appropriate shear forces and temperature conditions;
the process comprising a condition in which:
the weight ratio of the precursors to the core material is from 5/95 to 25/75; thereby obtaining microcapsules having 96% to 99% w/w of said core material.

13. The process of claim 12 further comprising a condition in which the concentration of the oily phase based on the total weight of the emulsion is from 50% to 90% w/w.

14. The process of claim 12 further comprising the step of mixing and stifling said emulsion with another aqueous solution at a suitably selected pH in the range 2-7, to obtain loaded microcapsules in a suspension.

15. The process of claim 12 wherein the pH of the aqueous solution is in the range 3-4.

16. The process of claim 12 comprising:
(a) mixing a core material and a precursor in a production reactor forming an oily phase;
(b) adding an aqueous phase having a pH in the range 2-7 to the production reactor in step (a) to form an oil-in water emulsion; and
(c) stirring the product obtained in step (b) until microcapsules are formed.

17. The process according to claim 12 wherein the process is conducted in one production reactor.

18. The process of claim 16 further comprising the step of adding an ingredient selected from a surfactant, a catalyst and a mixture thereof after step (b).

19. The process of claim 18 further comprising the step of diluting with an aqueous diluent after adding said ingredient.

20. The process of claim 18 wherein said catalyst is an acidic solution.

21. The process of claim 12 further comprising the step of isolating and rinsing the microcapsules through procedures selected from at least one of: separation by centrifuge; filtration; evaporation; re-suspension in aqueous medium; and dialysis.

22. The process of claim 12 further comprising the step of removing the water to obtain the final product in a powder form.

23. The process of claim 12 wherein the weight ratio of the precursors to the core material is from 10/90 to 15/85.

24. The process of claim 12 wherein the weigh weight ratio of the precursors to the core material is from 10/90 to 15/85 and the pH of said aqueous solution is 3-4.

25. The process of claim 12 wherein the active ingredient is selected from sunscreen agents, dental agents, fragrances, perfume, colors and dyes, food colors, food additives, waxes, antioxidants, humidifiers, vitamins, explosives, pesticides, biological molecules, drugs, catalysts, reagents, and mixtures thereof.

26. The process of claim 25 wherein said drug is selected from dermatological agents, anti-inflammatory agents, analgesics, anti-fungal agents, anti-biotics, anti-viral agents, anti-acne agents, anti histamines, skin whitening agents, anti-parasitic agents, muscle relaxants, steroids, hormones, astringents, and mixtures thereof.

27. The process of claim 25 wherein said sunscreen agent is selected from octylmethoxy cinnamate, 3-butylmethoxy-dibenzoyl methane, benzophenone-3, benzophenone-1, benzophenone-2, benzophenone-4, benzophenone-6, benzophenone-8, 2-ethylhexyl p-methoxycinnamate, p-aminobenzoic acid, 2-ethylhexyl N,N-dimethyl-p-aminobenzoate, 2-cyano-3,3-diphenylacrylic acid 2-ethylhexyl ester, 2-ethylhexyl-2-cyano-3,3-diphenylacrylate, oxybenzone, 2-phenylbenzimidizole-5-sulfonic acid, homomethyl salicylate, octyl salycilate, 4,4'-methoxy-t-butyldibenzoylmethane, 4-isopropyl dibenzoylmethane, 3-(4-methylbenzyledene) camphor, 3-benzylidene camphor, triethanolamine salicylate, 4-N,N-(2-ethylhexyl)methyl aminobenzoic acid ester of 2,4-dihydroxybenzophenone, 4-N,N-(2-ethylhexyl)methyl aminobenzoic acid ester of 4-hydroxydibenzoylmethane, 4-N,N-(2-ethylhexyl)methyl-aminobenzoic acid ester of 2-hydroxy-4-(2-hydroxyethoxy)-benzophenone, 4-N,N-(2-ethylhexyl) methyl aminobenzoic acid ester of 4-(2-hydroxyethoxy) dibenzoylmethane, and mixtures thereof.

28. The process of claim 25 wherein said dye is a fluorescent dye.

29. The process of claim 12 wherein said precursors are selected from silicon alkoxide monomers, silicon ester monomers, monomers of the formula $Si(R)_n(P)_m$, where R is a hydrolysable substituent, n is an integer from 2 to 4, P is a non polymerizable substituent and m is an integer from 0 to 4, a partially hydrolyzed and partially condensed polymer thereof, and any mixture thereof.

30. The process of claim 12 wherein said semi metal alkoxide monomer is silicon alkoxide monomer.

31. The process of claim 30 wherein said silicon alkoxide monomer is selected from tetramethoxy silane, tetraethoxy silane, and mixtures thereof.

32. The process of claim 30 wherein said silicon alkoxide monomer is tetraethoxy silane.

33. The process of claim 12 wherein said active ingredient is a sunscreen agent and said precursor is tetraethoxy silane.

* * * * *